United States Patent [19]

Crawford

[11] Patent Number: 5,526,677
[45] Date of Patent: Jun. 18, 1996

[54] SINGLE SENSOR DENSITY MEASURING APPARATUS AND METHOD

[75] Inventor: Ferdon H. Crawford, Elkhart, Ind.

[73] Assignee: Serim Research Corporation, Elkhart, Ind.

[21] Appl. No.: 371,148

[22] Filed: Jan. 11, 1995

[51] Int. Cl.⁶ ........................................ G01N 9/32
[52] U.S. Cl. ............................................ 73/32 R
[58] Field of Search ................... 73/32 R, 54.15, 73/64.52; 356/28, 72; 422/102

[56] References Cited

U.S. PATENT DOCUMENTS

| | | | |
|---|---|---|---|
| 2,166,842 | 7/1939 | Kagan | 73/32 R |
| 3,713,327 | 1/1973 | Clemens | 73/32 R |
| 4,646,562 | 3/1987 | Cronan | 73/64.52 |
| 4,843,869 | 7/1989 | Levine | 73/61.43 |
| 4,852,388 | 8/1989 | Park | 73/32 R |
| 4,952,054 | 8/1990 | Levine | 356/39 |
| 4,953,975 | 9/1990 | Levine | 356/246 |
| 5,141,310 | 8/1992 | Boiarski | 356/133 |
| 5,321,975 | 6/1994 | Levine | 73/61.71 |

OTHER PUBLICATIONS

The Sedimenting–Droplet Procedure For Measuring Fluid Densities, By A. Polson et al, Analytical Biochemistry 1980.
Settling Of Fixed Eryhrocyte Suspension Droplets, By, S. N. Omenyi et al, Biorheology, 20: 109–118, 1983.
Measurement Of Brain Tissue Specific Gravity Using Pycnometry, By G. Diresta et al, Journal of Neuroscience Methods, 1991.

A. Column Radioassay For The Quantification Of Vitamin B–12, By R. C. Boguslaski et al, Clinica Chimica Acta, 62 (1975).

Mettler Brochure On "Density/Specific Gravity Meters, DA–310/300", No Date Provided.

Anton Paar USA Brochure On "DMA48 Digital Density Meter", No Date Provided.

*Primary Examiner*—Hezron E. Williams
*Assistant Examiner*—Christine K. Oda
*Attorney, Agent, or Firm*—Baker & Daniels

[57] ABSTRACT

A method and apparatus for measuring the density or specific gravity of a fluid sample uses a single sensor. A reservoir contains another fluid of known density which is not miscible with the fluid sample. Sensors are disposed proximate to the reservoir to detect the passage of the fluid sample through the non-miscible fluid medium. A microprocessor monitors the sensor and calculates the specific gravity of the fluid sample. The microprocessor measures the amount of time one sensor is eclipsed as the fluid sample droplet falls through the fluid medium and calculates the density or specific gravity based on that amount of time. The microprocessor also may measure a second amount of time, the time required for the fluid sample to traverse through the fluid medium between two sensors. The microprocessor can use this second amount of time to measure the fluid droplet diameter or size. The microprocessor corrects the calculated density or specific gravity for any deviation caused by the size of the fluid sample.

22 Claims, 2 Drawing Sheets

SINGLE SENSOR DENSITY MEASURING APPARATUS AND METHOD

BACKGROUND OF THE INVENTION

1. Field of the Invention

The invention involves a method and apparatus for determining the density or specific gravity of a fluid. More particularly, the present invention relates to the determination of hemoglobin concentration in blood using a specific gravity method and apparatus.

2. Description of the Related Art

The measurement of density and specific gravity has application in many areas of Science, Engineering, Manufacturing, and Quality Assurance. Applications range from indirect measurement of the concentration of analytes in biological fluids, such as blood, saliva, and urine, to using the measurement of specific gravity or density to monitor the process quality of products such as foods, beverages, cosmetics, soaps, paints, and pigments. The measurement of density or specific gravity is also used indirectly to determine other process units such as alcohol degree, milk degree, Brix and API density in product processes.

The measurement of the density or specific gravity of fluids is important, and sometimes critical, for medical analysis and treatment. The density of a fluid is related to several physical properties of the fluid, including its specific gravity which is defined as the ratio of the density of the particular fluid to the density of water. For example, various body fluids, such as blood, urine, or cranial fluid, can be analyzed for their specific gravity to determine other pertinent physical properties. Thus, the analyte concentration of blood can be measured using its specific gravity to determine the amount of hemoglobin in blood or protein in the serum.

Several constraints complicate the measurement of specific gravity of body fluids. One constraint involves the difficulty or discomfort associated with obtaining the body fluid samples. Another constraint involves the criticality of the accuracy of the analyte concentration determination, because physicians select treatments for individuals based on the determined analyte concentrations. A further constraint involves the limited amount of body fluid which may be safely extracted from an individual. These and other constraints require that the measurement be accurate while only needing a small sample.

Conventional methods for measuring density or specific gravity use many different technologies. A common technology involves the manual manipulation of hydrometers, picnometers, and density determination kits using precise weight measurements. Digital density meters are also known to use either refractive index measurement or natural oscillation measurement technology.

Another known method of measuring specific gravity involves measuring the time of fall of a drop of fluid as it falls a fixed distance between two positions through another fluid of known specific gravity, which is termed the "falling drop" method. The "falling drop" method has thus far only received limited application due to the necessity to control the volume of the drop in order to obtain accurate specific gravity measurements. The drop must be non-miscible with the fluid medium, that fluid medium having a relatively low viscosity and a specific gravity lower than that of the drop. The drop must have a precisely dispensed volume which is introduced into the fluid medium below its surface. The non-miscible fluid being measured tends to form a drop in the form of a sphere. The descent of the drop through the fluid medium over a measured distance may be timed by a clinician. Automatic systems are also known which have two photosensors connected to a microprocessor with a timer so that the time of fall between the two sensors may be measured and calibrated against measurements of known specific gravity solutions.

The velocity or rate of fall of the spherical drop through the fluid medium is a function of the specific gravities of the drop and fluid medium, the viscosity of the fluid medium, the size of the drop, and the diameter of the tube containing the fluid medium. For a drop of approximately 35 microliters at terminal velocity in a 16 mm tube, time and distance are used in the following equation to calculate the specific gravity of the fluid:

$$SG_f = SG_m + \Delta SG_f, \Delta SG_f = \frac{K_1}{K_2} \cdot (visc) \cdot \frac{1}{d} \cdot \frac{D}{T_1}$$

where $SG_f$ is the specific gravity of the drop, $SG_m$ is the specific gravity of the fluid medium, $\Delta SG_f$ is the difference in specific gravity between the drop and the fluid medium, (visc) is the viscosity of the fluid medium, $K_1$ is a constant related to physical properties of the drop, tube diameter, and fluid medium, $K_2$ is $2/3\ \pi$, d is the diameter of the drop, D is the distance of fall through which the drop was timed, and T is the time the drop took to fall through the fluid medium over the predetermined distance. The disadvantage of this "between sensor falling drop" method of specific gravity measurement is that the measured specific gravity is inversely proportional to the diameter or size of the drop. Hence, it is necessary to dispense a precise size drop (volume of sample) to obtain accurate specific gravity measurement.

Although a precise performance of the "between sensor falling drop" method provides an accurate measurement of specific gravity, many difficulties are encountered in precisely performing the required measurements. One difficulty involves the precision of the volume of the drop being measured, because the volume is directly related to the diameter. As the diameter of the drop is a component of the specific gravity calculation above, the volume of the drop must be carefully controlled by dispensing the drop via a pipette under the surface of the fluid medium.

It is difficult and inconvenient for an analyst to dispense precise volumes. In the industrial setting, vibration and other factors may interfere with precise measurements. In the medical setting, the technicians may not have extensive training in precisely measuring the sample fluid. In addition, dispensing the drop under the surface of the fluid medium may result in trapped air bubbles which interferes with the accurate measurement of density or specific gravity. Another problem in dispensing under the fluid surface is that any electrostatic charge on the pipette tip is transferred to the oil and drop, and the charge on the materials thus effects the velocity and direction of the falling drop. This changes the drop fall time and can create errors in the density or specific gravity measurement. Also, conventional low cost transfer pipettes cannot consistently dispense a precise amount of fluid, and the size of the drop may vary from less than 20 microliters to as much as 50 microliters or more. This variability creates a corresponding variability in the specific gravity measurement.

What is needed is a density or specific gravity measurement method and apparatus which eliminates the variability of the measurements.

Also needed is a density or specific gravity measurement method and apparatus which allows for the sample to be dispensed conveniently above the fluid medium's surface.

SUMMARY OF THE INVENTION

The present invention is a method and apparatus using a single sensor to more accurately determine the specific gravity of a fluid. By timing the descent of a fluid through another nonmiscible fluid of a known specific gravity, the single sensor method measures the time for the fluid drop to traverse or eclipse the single sensor The present invention then calculates the specific gravity of the fluid based on the measured time of the sensor and the known specific gravity of the other fluid. The gross measurement variations resulting from the volume variability of the conventional falling drop method are eliminated by the present invention's single sensor method.

The apparatus includes a reservoir containing the second nonmiscible fluid into which a droplet of the fluid being tested is introduced. A sensor, such as a light sensor matched with a light source, is associated with the reservoir at a specific location or point. When the droplet passes through the nonmiscible fluid in front of the sensor, the sensor is activated. A processor with a timer measures the amount of time which transpires as the droplet eclipses the sensor while descending through the reservoir's fluid. With the present invention, the actual droplet size is no longer a factor in the determination of specific gravity because the measured time represents both the distance the droplet descended and the diameter of the droplet.

In addition to eliminating the measurement variations caused by volume variability, the present invention may use a second sensor to refine the measured time to account for variations in the descent time caused by a nontypical relationship between the reservoir size and the droplet size. For example, for small droplets, e.g. under 20 microliters, a lack of friction against the sides of the reservoir may allow the droplet to descend faster than a larger droplet. Even larger droplets can become a problem if the droplet increases in size such that the sides of the reservoir create an additional drag slowing down the droplet. A correction equation, such as a second order equation, may be used by the processor to correct the timing measurement to compensate for droplets that are too large or too small before calculating the specific gravity.

A second order equation provides an sufficient adjustment for correcting the timing measurement. Alternatively, a first order equation, a higher order equation, or an empirically determined look up table may be used to perform the desired correction. In fact, the correction for volume variations may be employed on the conventional between sensor specific gravity calculation, which for some applications may be preferable.

The present invention provides several advantages. The accuracy of the specific gravity measurements are, at the least, equivalent to that of prior art methods. The resulting apparatus is simple and easily used, the user need only to introduce an unmeasured volume of fluid sample into the reservoir above the fluid to obtain the desired reading. The processor automatically monitors the sensor and displays the calculated specific gravity, or any other calculated amount related to specific gravity. The sensor and processor may be operated on batteries, and thus the machine is portable. The measured fluid samples simply accumulate in the bottom of the reservoir which can be easily and safely removed for disposal.

The present invention, in one form, involves a method of calculating the specific gravity of a first fluid. The method involves providing a second fluid, introducing the first fluid into the second fluid, timing, and calculating. The second fluid is of known specific gravity and is not miscible with the first fluid. The amount of time required for the first fluid to traverse through the second fluid at a predetermined location or point is then measured. Finally, the specific gravity is calculated according to the measured amount of time.

The present invention, in another form, involves an apparatus for measuring the specific gravity of a first fluid. The apparatus comprises a reservoir, sensors, and a calculator. The reservoir contains a second fluid of known specific gravity which is not miscible with the first fluid. Each sensor is operably associated with the reservoir. The calculator determines the specific gravity of the first fluid, and is connected to the sensors. The calculator includes a device for measuring a first amount of time of the activation of one of the sensors. The calculator also includes means for measuring a second amount of time required for the first fluid to traverse through the second fluid between the sensors. The calculator calculates the specific gravity according to the first measured amount of time and the second measured amount of time.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates preferred embodiments of the invention, in several forms, and such exemplifications are not to be construed as limiting the scope of the invention in any manner.

DESCRIPTION OF THE PREFERRED EMBODIMENTS

The preferred embodiments disclosed below are not intended to be exhaustive or limit the invention to the precise forms disclosed in the following detailed description. Rather, the embodiments are chosen and described so that others skilled in the art may utilize their teachings.

The disclosed embodiment of the invention is a hemoglobinometer which is designed to measure the specific gravity of a blood sample and display a number representing either the hemoglobin content or a percentage hematocrit of the blood sample. However, the general techniques of the method and apparatus described below may be applied to many other fields such as scientific instruments, engineering, manufacturing, and quality assurance testing. Applications range from indirect measurement of the concentration of analytes in biological fluids, such as blood, saliva, and urine, to using the measurement of specific gravity or density to monitor the process quality of products such as foods, beverages, cosmetics, soaps, paints, and pigments. The measurement of density or specific gravity is also used indirectly to determine other process units such as alcohol degree, milk degree, Brix and API density in product processes.

Figure 1:
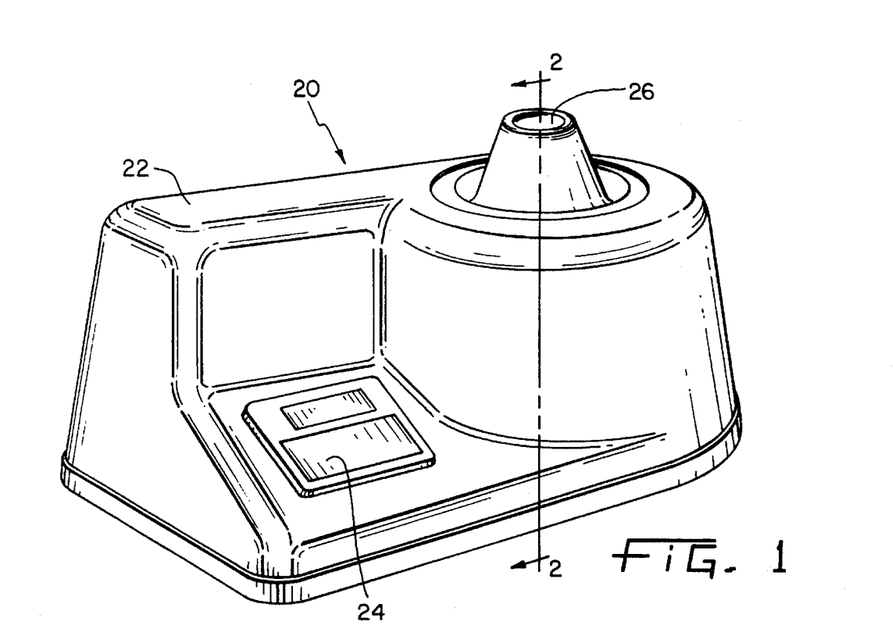
FIG. 1 is a perspective view of the hemoglobinometer of the present invention.
Figure 2:
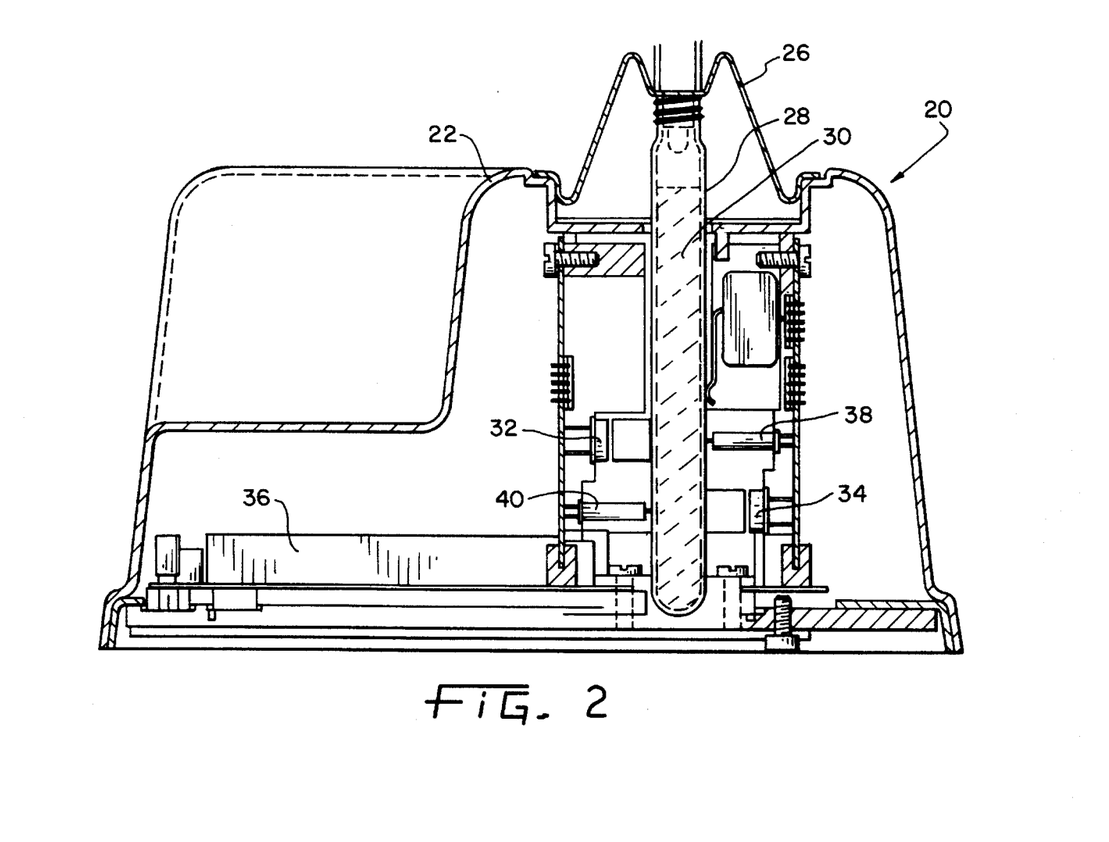
FIG. 2 is a sectional view of the hemoglobinometer taken along view lines 2—2 of FIG. 1.

FIG. 1 shows a perspective view of a hemoglobinometer which operates according to the present invention. Hemoglobinometer 20 is a self-contained unit with housing 22, display 24, and sample portal 26. The clinician introduces a drop of a blood sample through portal 26, and using one of the methods described below then presents the hemoglobin content or percentage hematocrit on display 24. As shown in FIG. 2, portal 26 may be removed from housing 22 for cleaning. Portal 26 is also removable from tube 28 so that tube 28 can be easily replaced by a clinician. Tube 28 contains a fluid 30, such as an oil, which has a lower specific gravity and is not miscible with blood. Through use of hemoglobinometer 20, tube 28 may also contain waste material (old blood samples) which settle to the bottom of tube 28 (see FIG. 4). By allowing removal of tube 28, a new tube may be inserted and the old tube capped and disposed of in a biological hazard container. In the disclosed embodiment, fluid 30 comprises a silicone oil with a specific gravity of approximately 0.93 and a viscosity of approximately 10 centistokes.

The specific gravity measurement, and the calculation of hemoglobin content, is performed by the devices within housing 22. In the exemplary embodiment, light sensors 32 and 34 are associated with tube 28 to monitor the descent of a drop of blood (not shown) through fluid 30. Although the disclosed embodiment uses light photo sensors, other sensor devices are possible such as sensors responsive to other types of radiation, sensors responsive to motion, sensors responsive to magnetic resonance, or other suitable sensor devices. Light sensors 32 and 34 are electrically coupled with circuit board 36 to monitor the material within tube 28. Light sources 38 and 40 are arranged on opposite sides of light sensors 32 and 34, respectively, so that when the sample fluid passes through the location of sensor 32 or 34, the sensor is activated which indicates the presence of the sample at that location or point. In the exemplary embodiment, light sources 38 and 40 comprise light emitting diodes (LED's).

Figure 3:
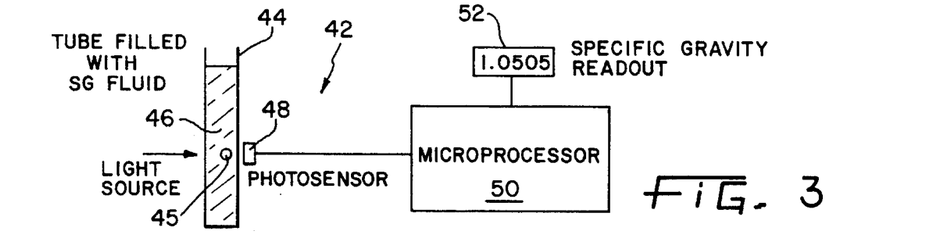
FIG. 3 is a schematic view of the single sensor hemoglobinometer.

Although the disclosed embodiment includes two light sensors, the present invention contemplates a device which uses only one sensor. The arrangement and operation of such a single sensor device is shown schematically in FIG. 3 and as a flow chart in FIG. 5. Referring to FIG. 3, hemoglobinometer 42 includes tube 44 with drop 45 in fluid 46, photosensor 48 with associated light source (not shown), microprocessor 50, and display 52. Photosensor 48 is disposed proximate tube 44 and is connected to microprocessor 50 so that the amount of time that photosensor 48 is activated may be measured, the specific gravity calculated, and the calculated amount of hemoglobin or percentage of hematocrit may be displayed on display 52.

Figure 5:
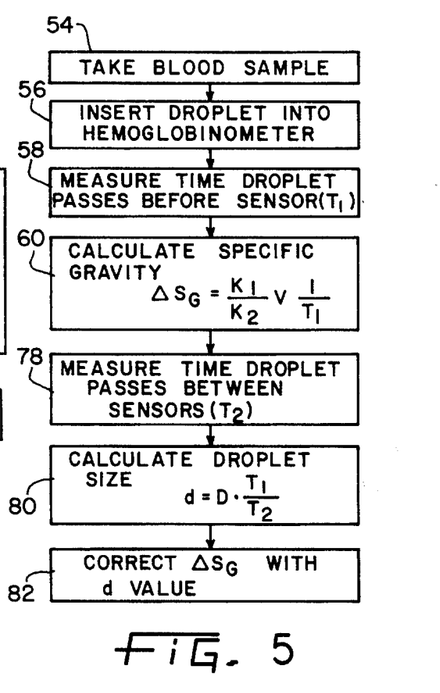
FIG. 5 is a flow chart of the operation of the hemoglobinometers.

Hemoglobinometer 42 operates according to steps 54–60 of FIG. 5. First, a clinician obtains a blood sample from a patient at step 54. The clinician then introduces drop 45 of the blood into portal 26 so that drop 45 starts to descend through tube 44 at step 56. Once drop 45 begins to descend through tube 44, a timer on circuit board 36 measures the time ($T_1$) required for drop 45 to pass the sensor at step 58. With the time elapsed from drop 45 passing in front of the sensor, the specific gravity may be calculated.

Circuit board 36, which includes a microprocessor and related circuitry, calculates the specific gravity according to the conventional "between sensor falling drop" equation. However, the conventional equation can be simplified because the distance which drop 45 descends while being monitored is its diameter. Given that the distance of the fall equals the drop diameter, the single sensor "falling drop" equation may be reduced to:

$$SG_f = SG_m + \Delta SG_f, \quad \Delta SG_f = \frac{K_1}{K_2} \cdot (visc) \cdot \frac{1}{d} \cdot \frac{d}{T_1}$$

which further simplifies to:

$$SG_f = SG_m + \Delta SG_f, \quad SG_f = \frac{K_1}{K_2} \cdot (visc) \cdot \frac{1}{T_1}$$

where $SG_f$ is the specific gravity of drop 45, $SG_m$ is the specific gravity of fluid 46, $\Delta SG_f$ is the difference in specific gravity between drop 45 and fluid 46, (visc) is the viscosity of fluid 46, $K_1$ is a constant related to physical properties of drop 45, the tube diameter, and fluid 46, $K_2$ is $\frac{2}{3}\pi$, d is the diameter of drop 45, and T is the time required by drop 45 to eclipse or pass sensor 48 while traversing through fluid 46. The calculated specific gravity of the blood sample is converted to a hemoglobin or percentage hematocrit and presented to the clinician via display 52.

The advantages of the method described above may be enhanced by using a second sensor to correct for sample drops which are significantly above or below preferred volumes. In the preferred volume range, e.g., 20 to 50 microliters, the friction forces from the tube wall counter balance some of the gravitational forces so that the resulting measurement is accurate when used with the exemplary embodiment wherein tube 28 has a 16 millimeter diameter. However for drops which are too small, e.g., less than 20 microliters, the fall time of the drop is less than with a volume in the preferred range because the friction forces from the tube wall are much less significant. Correspondingly, for drops which are too large, e.g., more than 50 microliters, the fall time of the drop is greater than with a volume in the preferred range because of the drag from the tube walls. The second, two sensor embodiment of the invention uses an empirically determined correction for drop size so that volumes outside the preferred range are also accurately determined.

Figure 4:
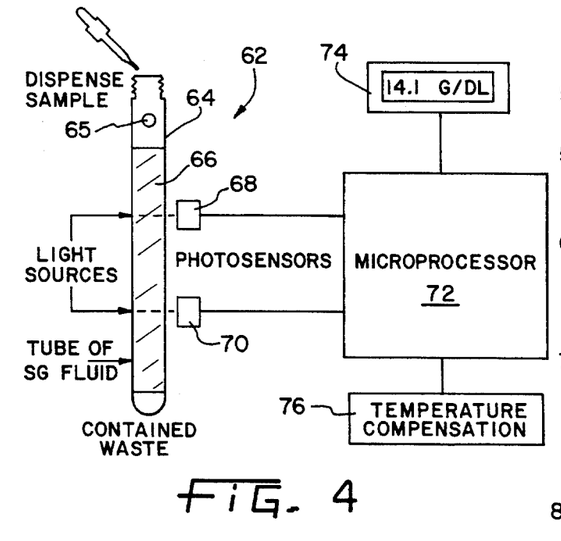
FIG. 4 is a schematic view of two sensor hemoglobinometer utilizing the second sensor for drop size correction.

The arrangement and operation of such two sensor device is shown schematically in FIG. 4 and as a flow chart in FIG. 5. Referring to FIG. 4, hemoglobinometer 62 includes tube 64 with drop 65 in fluid 66, photosensors 68 and 70 with associated light sources (not shown), microprocessor 72, and display 74. Photosensors 68 and 70 are disposed proximate tube 64 and are connected to microprocessor 72 so that the amount of time that photosensors 68 and 70 activated may be measured, the specific gravity calculated, and the calculated amount of hemoglobin or percentage of hematocrit may be displayed on display 74. Additionally, temperature compensation device 76 may be included, which monitors the temperature of fluid 66 so that the calculations performed by microprocessor 74 may include a compensation for the ambient temperature, e.g., adjusting the constants and viscosity factors in the specific gravity equation according to the temperature.

Hemoglobinometer 62 may operate according to steps 54–60 and 78–82 of FIG. 5. After steps 54–60 are performed as disclosed above, microprocessor additionally measures the amount of time ($T_2$) required for drop 65 to fall between photosensors 68 and 70 at step 78. As the velocity of drop 65 should be constant as it flows through fluid 66, the velocity at the location of photosensor 68 ($d/T_1$) [where d is the diameter of drop 65] is equal to the velocity when traversing from photosensor 68 to photosensor 70 ($D/T_2$) [where D is the distance between photosensors 68 and 70]. Setting these two expression equal results in the size of drop 65 being equal to the distance between the photosensors multiplied by $T_1/T_2$. Calculating the size of drop 65 at step 80 allows the use of a correction table or equation in step 82 to correct the calculation of the specific gravity of the sample.

Alternatively, steps 54–58 and steps 78–80 may be independently performed, and the determined drop size used in a correction function to supply the specific gravity calculation of step 60 with a corrected time value. The correction function may a single order equation, a second order equation, a higher order equation, or an empirically generated lookup table. For example, the following second order equation has been empirically determined to correct for a 16 millimeter diameter tube:

$$T_c = T_1(1 - 0.022(d - 4.25)^2)$$

where $T_1$ is as defined above, $T_c$ is the corrected time value to be used in the equation of step 60 to calculate the specific gravity, 0.022 is a constant empirically determined from a best fit analysis of a set of sample runs of hemoglobinometer 62, d is the diameter as determined in step 80. The constant 4.25 is the nominal measured diameter of a drop that is typically about 35 microliters. The constant 0.022 was empirically derived from data using a 16 millimeter tube and drop sizes ranging from 10 to 100 microliters. These constants were selected to obtain the best fit to the second order equation.

Figure 6:
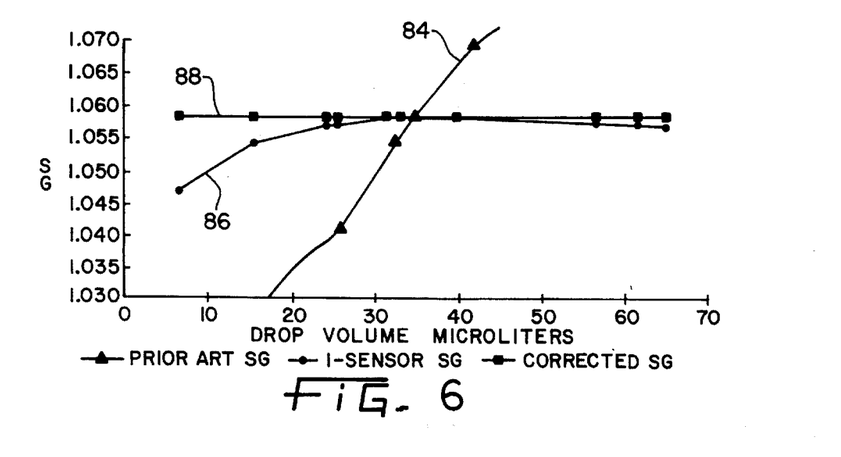
FIG. 6 is a graph of specific gravity data comparing single sensor specific gravity methods with the prior art "between sensor falling drop" method.

The improved performance of the present invention is shown in the graph of FIG. 6. The graph of FIG. 6 plots the drop size of several samples of known specific gravity against the measured specific gravity (the known specific gravity being about 1,058 in this example). The prior art between sensor specific gravity (SG) device is only accurate at a drop volume of about 35 microliters, as line 84 of the graph shows. With the single sensor embodiment of the invention, as shown in line 86, the hemoglobinometer is highly accurate within a range of drop sizes from 20 to 50 microliters. The accuracy of the single sensor hemoglobinometer is suitable for many clinical applications, as the 20 to 50 microliter range is fairly easy for a clinician to dispense. However, for best results the second sensor size corrected specific gravity measurement of the second embodiment of the invention, represented by line 88, is accurate at all points of the graph of FIG. 6.

While this invention has been described as having a preferred design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of determining the density or specific gravity of a first fluid comprising the steps of:

providing a second fluid of known density or specific gravity which is not miscible with the first fluid;

introducing the first fluid into the second fluid;

measuring the time required for the first fluid to traverse through the second fluid at a predetermined point; and calculating the density or specific gravity according to the measured amount of time.

2. The method of claim 1 further comprising the step of measuring the size of a droplet of the first fluid in the second fluid wherein said calculating step includes calculating the density or specific gravity according to the measured amount of time and the measured volume of the first fluid.

3. The method of claim 1 wherein said calculating step calculates the density or specific gravity of the first fluid according to the equation:

$$SG_1 = SG_2 + \frac{K_1}{K_2} \cdot (visc) \cdot \frac{1}{T_1}$$

where $SG_1$ is the density or specific gravity of the first fluid, $SG_2$ is the density or specific gravity of the second fluid, (visc) is the viscosity of the second fluid, $K_1$ is a constant related to the first fluid, $K_2$ is a constant related to the second fluid, and T is the measured amount of time.

4. The method of claim 1 further comprising the step of measuring a second amount of time required for the first fluid to traverse a predetermined distance and said calculating step includes a correcting step using the second measured time to calculate the size of a droplet of the first fluid and correct the calculated density or specific gravity according to the calculated droplet size of the first fluid.

5. The method of claim 1 further comprising the step of measuring a second amount of time required for the first fluid to traverse a predetermined distance and said calculating step includes a correcting step using the second measured amount of time to correct for measurement variations.

6. The method of claim 5 wherein said correcting step determines a corrected time for calculating the density or specific gravity using the equation:

$$T_c = T(1 - A \cdot (d - B)^2)$$

where $T_c$ is the corrected time for the density or specific gravity calculation, T is the measured amount of time, A is a constant, d is the diameter of the first fluid, and B is a constant.

7. The method of claim 6 wherein said correcting step determines the diameter of the first fluid using the equation:

$$d = D \cdot (T/T_2)$$

where D is the predetermined distance which the first fluid traversed, T is the measured amount of time, and $T_2$ is the second measured amount of time.

8. The method of claim 4 wherein said correcting step uses a look up table of values to correct for measurement variations.

9. The method of claim 4 wherein said calculating step calculates the density or specific gravity of the first fluid according to the equation:

$$SG_1 = SG_2 + \frac{K_1}{K_2} \cdot (visc) \cdot \frac{1}{d} \cdot \frac{D}{T_2}$$

where $SG_1$ is the density or specific gravity of the first fluid, $SG_2$ is the density or specific gravity of the second fluid, (visc) is the viscosity of the second fluid, $K_1$ is a constant related to the first fluid, $K_2$ is a constant related to the second fluid, d is the diameter of the first fluid derived from the calculated size of the first fluid, D is the predetermined distance, and $T_2$ the second measured amount of time.

10. An apparatus for measuring the density or specific gravity of a first fluid comprising:

a reservoir containing a second fluid of known density or specific gravity and which is not miscible with the first fluid;

a sensor operably associated with said reservoir, said sensor being activated by the first fluid traversing through said second fluid at a predetermined location point in said reservoir; and means for calculating the density or specific gravity of the first fluid, said calculating means being connected to said sensor and including means for measuring the amount of time of the activation of said sensor and thereby measure the amount of time required for the first fluid to traverse through said second fluid at the predetermined location, said calculating means calculating the density or specific gravity according to the measured amount of time.

11. The apparatus of claim 10 wherein said reservoir is detachable from said apparatus.

12. The apparatus of claim 10 wherein said calculating means calculates the density or specific gravity of the first fluid according to the equation:

$$SG_1 = SG_2 + \frac{K_1}{K_2} \cdot (visc) \cdot \frac{1}{T_1}$$

where $SG_1$ is the density or specific gravity of the first fluid, $SG_2$ is the density or specific gravity of said second fluid, (visc) is the viscosity of said second fluid, $K_1$ is a constant related to the first fluid, $K_2$ is a constant related to said second fluid, and T is the measured amount of time.

13. The apparatus of claim 10 further comprising means for measuring a second amount of time required for the first fluid to traverse a predetermined distance, and said calculating means includes means for correcting the calculated density or specific gravity using the second measured time to calculate the size of a droplet of the first fluid and correct the calculated density or specific gravity according to the calculated droplet size of the first fluid.

14. The apparatus of claim 13 wherein said correcting means includes means for measuring a second amount of time required for the first fluid to traverse a predetermined distance and said correcting means uses said second measured amount of time to correct for measurement variations.

15. The apparatus of claim 14 wherein said correcting means determines a corrected measured time for said calculating means using the equation:

$$T_c = T(1 - A \cdot (d-B)^2)$$

where $T_c$ is the corrected measured time for the specific gravity calculation, T is the measured amount of time, and A is a constant, d is the diameter of the first fluid, and B is a constant.

16. The apparatus of claim 15 wherein said correcting means determines the diameter of the first fluid using the equation:

$$d = D \cdot (T/T_2)$$

where D is the predetermined distance which the first fluid traversed, T is the measured amount of time, and $T_2$ is the second measured amount of time.

17. The apparatus of claim 14 wherein said correcting means includes a look up table of values to correct for measurement variations.

18. The apparatus of claim 15 wherein said calculating means calculates the density or specific gravity of the first fluid according to the equation:

$$SG_1 = SG_2 + \frac{K_1}{K_2} \cdot (visc) \cdot \frac{1}{d} \cdot \frac{D}{T_2}$$

where $SG_1$ is the density or specific gravity of the first fluid, $SG_2$ is the density or specific gravity of said second fluid, (visc) is the viscosity of said second fluid, $K_1$ is a constant related to the first fluid, $K_2$ is a constant related to said second fluid, d is the diameter of the first fluid derived from the calculated size of the first fluid, D is the predetermined distance which the first fluid traversed, and $T_2$ is the second measured amount of time.

19. An apparatus for measuring the density or specific gravity of a first fluid comprising:

a reservoir containing a second fluid of known density or specific gravity and which is not miscible with the first fluid;

a first and second sensor, each said sensor being operably associated with said reservoir; and means for calculating the density or specific gravity of the first fluid, said calculating means being connected to said first and second sensor and including means for measuring a first amount of time of the activation of one of said first sensor and said second sensor, said calculating means also including means for measuring a second amount of time required for the first fluid to traverse through said second fluid between said first sensor and said second sensor, said calculating means calculating the density or specific gravity according to the first measured amount of time and the second measured amount of time.

20. The apparatus of claim 19 wherein said calculating means uses the second measured amount of time in a second order equation to correct for measurement variations caused by variations of the amount of the first fluid and thereby calculating a corrected measured amount of time.

21. The apparatus of claim 19 wherein said calculating means calculates the density or specific gravity of the first fluid according to the equation:

$$SG_1 = SG_2 + \frac{K_1}{K_2} \cdot (visc) \cdot \frac{1}{T_1}$$

where $SG_1$ is the density or specific gravity of the first fluid, $SG_2$ is the density or specific gravity of said second fluid, (visc) is the viscosity of said second fluid, $K_1$ is a constant related to the first fluid, $K_2$ is a constant related to said second fluid, and T the measured amount of time.

22. The apparatus of claim 19 wherein said calculating means calculates the density or specific gravity of the first fluid according to the equation:

$$SG_1 = SG_2 + \frac{K_1}{K_2} \cdot (visc) \cdot \frac{1}{d} \cdot \frac{D}{T_1}$$

where $SG_1$ is the estimated density or specific gravity of the first fluid, $SG_2$ is the density or specific gravity of said second fluid, (visc) is the viscosity of said second fluid, $K_1$ is a constant related to the first fluid, $K_2$ is a constant related to said second fluid, d is the diameter of the first fluid droplet, D is the predetermined distance which the first fluid traversed, and T is the corrected amount of time; and said calculating means further calculates the density or specific gravity according to the estimated density or specific gravity and a calculated size of the first fluid, said calculating means determining the calculated size of the first fluid by the equation:

$$d = D \cdot (T_1/T_2)$$

where d is the diameter of the first fluid droplet, D is the distance between said first sensor and said second sensor, $T_1$ is the measured amount of time, and $T_2$ is the second measured amount of time.

* * * * *

UNITED STATES PATENT AND TRADEMARK OFFICE
CERTIFICATE OF CORRECTION

PATENT NO. : 5,526,677
DATED : June 18, 1996
INVENTOR(S) : Ferdon H. Crawford

It is certified that error appears in the above-indentified patent and that said Letters Patent is hereby corrected as shown below:

Claim 3, column 8, line 22, change "T" to --$T_1$--.

Claim 6, column 8, line 40, change "T" to --$T_1$--.

Claim 6, column 8, line 43, change "T" to --$T_1$--.

Claim 7, column 8, line 49, change "T" to --$T_1$--.

Claim 7, column 8, line 52, change "T" to --$T_1$--.

Claim 10, column 9, line 12, delete "location".

Claim 12, column 9, line 35, change "T" to --$T_1$--.

Claim 15, column 9, line 52, change "T" to --$T_1$--.

Claim 15, column 9, line 56, change "T" to --$T_1$--.

Claim 16, column 9, line 62, change "T" to --$T_1$--.

UNITED STATES PATENT AND TRADEMARK OFFICE
CERTIFICATE OF CORRECTION

PATENT NO. :   5,526,677
DATED      :   June 18, 1996
INVENTOR(S) :  Ferdon H. Crawford It is certified that error appears in the above-indentified patent and that said Letters Patent is hereby corrected as shown below:

Claim 16, column 9, line 66, change "T" to --$T_1$--.

Claim 21, column 10, line 55, change "T" to --$T_1$--.

Claim 22, column 11, line 3, change "T" to --$T_1$--.

Signed and Sealed this

Fifteenth Day of October, 1996

BRUCE LEHMAN

Attest:

*Attesting Officer*     *Commissioner of Patents and Trademarks*